United States Patent [19]

Schinazi et al.

[11] Patent Number: 5,462,724
[45] Date of Patent: Oct. 31, 1995

[54] SENSITIZING AGENTS FOR USE IN BORON NEUTRON CAPTURE THERAPY

[76] Inventors: Raymond F. Schinazi, 1524 Regency Walk Dr., Decatur, Ga. 30033; Dennis C. Liotta, 251 Montrose Dr., McDonough, Ga. 30253-4243

[21] Appl. No.: 380,520

[22] Filed: Jan. 30, 1995

Related U.S. Application Data

[62] Division of Ser. No. 840,093, Feb. 24, 1992, Pat. No. 5,405,598.

[51] Int. Cl.⁶ .................. A61K 31/69; C07F 9/12
[52] U.S. Cl. .................. 424/1.77; 514/64; 558/72
[58] Field of Search .................. 558/72; 514/64; 424/1.77

[56] References Cited

U.S. PATENT DOCUMENTS

| | | | |
|---|---|---|---|
| H505 | 8/1988 | Slatkin et al. | 424/1.61 |
| 4,959,356 | 9/1990 | Miura et al. | 424/1.81 |
| 5,021,572 | 6/1991 | Gabel | 544/229 |
| 5,066,479 | 11/1991 | Hawthorne | 424/1.53 |

*Primary Examiner*—Johann Richter
*Assistant Examiner*—Michael G. Ambrose
*Attorney, Agent, or Firm*—Oblon, Spivak, McClelland, Maier & Neustadt

[57] ABSTRACT

Compounds of formula I and II

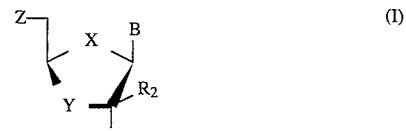

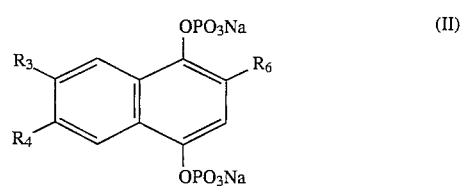

in which B contains a carboranyl group and one of $R_3$ and $R_4$ is a carboranyl group or a boronic acid or ester are useful sensitizing agents for boron neutron capture therapy.

7 Claims, No Drawings

SENSITIZING AGENTS FOR USE IN BORON NEUTRON CAPTURE THERAPY

This is a division of application Ser. No. 07/840,093 filed on Feb. 24, 1992 now U.S. Pat. No. 5,405,598.

BACKGROUND OF THE INVENTION

1. Field of the Invention

The present invention relates to novel sensitizing agents for boron neutron capture therapy and therapeutic methods which employ such sensitizing agents.

2. Discussion of the Background

According to the American Association For Brain Tumor, in the United States alone about 20,000 persons develop brain tumors yearly. The most common type of brain tumor is the glioma with an incidence ranging from 31% to 49% of all intracranial tumors and a mortality of greater than 99% in such individuals no matter how radical the surgical procedure. In individuals suffering from such tumors, survival time is usually measured in weeks or months rather than in years.

Gliomas are characterized by a main tumor mass with finger-shaped colonies of neoplastic cells that invade surrounding brain tissue and are dispersed. These tumors are often inaccessible to surgical removal or to standard external beam therapy. The encouraging clinical results with neutron capture therapy (NCT) of glioblastoma using a sulfhydryl borane monomer and continued interest in the preparation of third generation boron compounds for NCT have provided considerable momentum for the treatment of brain and other tumors using this therapeutic modality.

The use of boron compounds for boron neutron capture therapy (BNCT) is a combined modality consisting of the interaction of two components, neutrons and $^{10}B$. Non-radioactive $^{10}B$ at 20% natural abundance, has a high neutron capture cross-section (3,850 barns). The $^{10}B$ nucleus absorbs a low energy thermal neutron releasing an alpha particle, a lithium atom, and about 100 million times more energy than that which was put in. Since the effect in human tissue is dependent upon both the boron concentration within the irradiated tissue and the total thermal neutron flux, cellular death is not a random phenomenon. Thus, a physical differential is obtained which is unavailable with conventional radiotherapy. None of the normal elements comprising human tissue possesses cross sections for thermal neutrons comparable to $^{10}B$. Because the nuclear fragments from the $^{10}B(n,\alpha)^7Li$ reaction travel only about 10 µm, destructive radiation predominates only in the immediate vicinity of cells having a high $^{10}B$ content. The thermal neutrons themselves are of subionizing energy and diffuse relatively harmlessly through tissue until captured by various elements. Thus, the potentially cytotoxic agent is non-toxic to the tumor cells until activated by an externally applied radiation field of neutrons. A major advantage of this binary system is that the time for irradiation can be selected so that the dose of irradiation can be delivered when the ratio of the concentration of the sensitizing agent in the tumor tissue to that in the normal tissue is optimal.

Although significant advances have been made in NCT, because of the inherent difficulty in synthesizing rationally designed hydrolytically stable boron compounds, it is clear that more emphasis should be placed on the chemical and pharmacological aspects. The thymidine analogue, 5-dihydroxyboryl-2'-deoxyuridine (DBDU), Schinazi and Prusoff, *J. Org. Chem.*, vol. 50, pp. 841–847, (1985) a compound has been shown to destroy hamster V-79 cells when irradiated with low energy neutrons. This destruction is a consequence of the $^{10}B(n,\alpha)^7Li$ reaction itself, as well as a concomitant self-sensitization to those radiations provided by the presence of the nucleoside analog in DNA.

The viability of 3'-heteranucleosides, such as racemic 2',3'-dideoxy-3'-thiacytidine (BCH-189) and 2',3'-dideoxy-5-fluoro-3'-thiacytidine (FTC), as both anti-human immunodeficiency viruses (HIV) and anti-Hepatitis B virus (HBV) agents has been demonstrated (Choi et al, *J. Amer. Chem. Soc.*, 113:9377–9379, 1991; Doong et al, *Proc. Natl. Acad. Sci. USA*, 88:8495–8499, 1991; Doong et al, Interscience Conference on Antimicrobial Agents and Chemotherapy, Chicago, Ill., Sep. 29–Oct. 2, 1991; Schinazi et al, National Collaborative Drug Discovery Group, Frontiers in HIV Therapy, San Diego, Calif., Nov. 3–7, 1991; Schinazi et al, *Antimicrob. Agents Chemother.*, 36 (3):1992 (in press); Unpublished results from Hoong et al).

These compounds not only show good activity against these viruses, but also exhibit extremely low toxicity. In addition, they readily permeate cell membranes, are excellent substrates for cellular kinases, and resist many other catabolic processes that are commonly observed with other 2'-deoxycytidine nucleosides (Schinazi et al, National Collaborative Drug Discovery Group, Frontiers in HIV Therapy, San Diego, Calif., Nov. 3–7, 1991).

Analogues of 6-iodo-2-methyl-1,4-naphthoquinol bis(diammonium phosphate) (6-I-MNDP) are known to selectively concentrate in the cells of some human malignant tumors (Brown et al, *Eur. J. Nucl. Med.*, 7(3):115–20, 1982; Carpenter et al, *Int. J. Radiat. Oncol. Biol. Phys.*, 9:51–5, 1983; Mitchell et al, *Prog. Clin. Biol. Res.*, 166:327–35, 1984; Mitchell et al, *Experientia*, 41:925–8, 1985). These synthetic water-soluble molecules are related chemically to vitamin K (Mitchell et al, *Nature*, 160:98–99, 1947). Uptake of 6-I-MNDP into malignant cells is significantly higher (15 to 20-fold) than in normal cells under both euoxic and hypoxic conditions (Brown et al, *Eur. J. Nucl. Mede*, 7(3):115–20, 1982; Carpenter et al, Int. *J. Radiat. Oncol. Biol. Phys,*, 9:51–5, 1983). In addition, α-particle track autoradiographic studies of radiolabeled 6-I-MNDP in mice have demonstrated low uptake into critical radiosensitive tissues, such as bone-marrow, colon, and lung, and high uptake in tumor tissues (Mitchell et al, *Experientia*, 41:925–8, 1985). The halogen-carbon bond in 6-I-MNDP is metabolically stable in mice. Mitchell (Mitchell, *Br. J. Cancer*, 29:373–88, 1974) performed studies with radiolabeled MNDP in 203 patients with different malignant tumors. High specific activity preparations were useful in the treatment of some patients with advanced tumors, especially carcinoma of the colon and pancreas and for malignant melanoma. The specificity of 6-I-MNDP has been attributed to the expression of oncogenically associated alkaline phosphatase isoenzyme in certain tumor cells and in particular cell-membrane bound enzyme.

Thus, there remains a need for sensitizing agents for boron neutron capture therapy.

SUMMARY OF THE INVENTION

Accordingly, it is one object of the present invention to provide novel sensitizing agents for boron neutron capture therapy.

It is another object of the present invention to provide an improved method of treating cancer by boron neutron capture therapy utilizing such a boron-containing sensitizing agent.

It is another object of the present invention to provide pharmaceutical compositions containing such boron neutron capture therapy sensitizing agents.

These and other objects, which will become apparent during the following detailed description, have been achieved by the inventors' discovery that compounds of the formulae

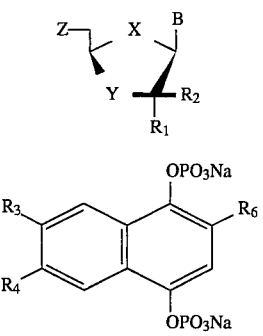

wherein: Z is OH, —OP(=O)(OH)$_2$, —OP(=O)(OH)OP(=O)(OH)$_2$, —OP(=O)(OH)OP(=O)(OH)$_2$, OR$_5$ (wherein R$_5$ is a hydroxy protecting group such as tri-C$_{1-4}$-alkylsilyl, di-C$_{1-4}$-alkylphenylsilyl, C$_{1-4}$-alkyl-diphenylsilyl, or trityl), —P(=O)(OH)$_2$, —P(=O)(OR$_6$)$_2$ (wherein R$_6$ is C$_{1-4}$-alkyl), —OR$_6$, R6NH—, R$_6$R$_6$N—, R$_6$C(=O)O—, —SH, or —SR$_6$;

X is O, S, NR' (wherein R' is H or C$_{1-4}$-alkyl) or CHR';

Y is O, S, NR' or CHR' (wherein R' has the same meaning given above);

R$_1$ and R$_2$ are: each, independently, H, C$_{1-4}$-alkyl, —CF$_3$, or —F;

B = a purine or pyrimidine base selected from the group consisting of:

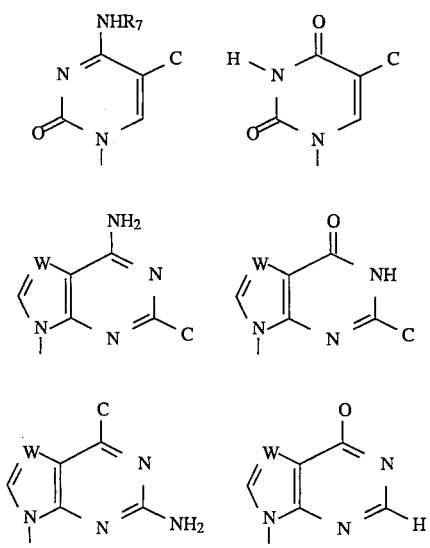

wherein C is a carboranyl group such as —B$_{10}$H$_{10}$C$_2$R$_8$, wherein R$_8$ is —H, —OH, —CH$_2$OH, —CH$_2$X (wherein X is F, Cl, Br, I) or—B$_9$C$_2$H$_{12}$⁻ (nidocarborane anion)

R$_7$ is C$_{1-4}$-alkyl or H;

W is N or CH; and

R$_3$ and R$_4$ are each, independently, —H, —B(OH)$_2$, —B(OR$_6$)$_2$, or a carboranyl group having the formula —B$_{10}$H$_{10}$C$_2$R$_8$, wherein R$_8$ is —H, —OH, —CH$_2$OH, —CH$_2$X (wherein X is F, Cl, Br, I) or —B$_9$C$_2$H$_{12}$⁻ (nidocarborane anion) provided that one of R$_3$ and R$_4$ is —H and the other of R$_3$ and R$_4$ is not —H, act as sensitizing agents for boron neutron capture therapy.

DETAILED DESCRIPTION OF THE PREFERRED EMBODIMENTS

Thus, in one embodiment, the present invention relates to sensitizing agents for boron neutron capture therapy having the formula I:

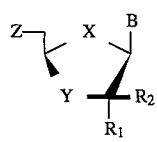

In which X, Y, Z, R$_1$, R$_2$, and B have the meanings described above. It is preferred that X is O and Y is S. It is also preferred that both R$_1$ and R$_2$ are —H. In addition, it is preferred that Z is —OH, a mono-, di-, or triphosphate group, or

It is further preferred that B is a group of the formula:

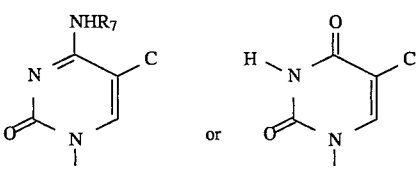

The synthesis of the compounds of the formula (I) when X is O and Y is S is outlined in scheme I shown below.

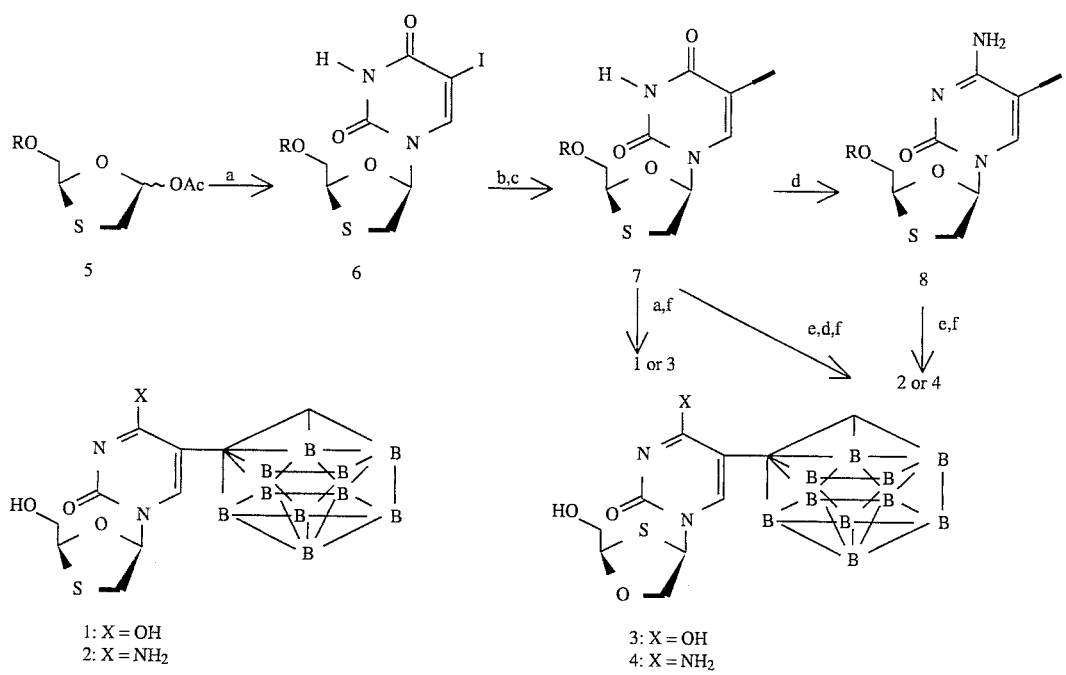

1: X = OH
2: X = NH₂

3: X = OH
4: X = NH₂

The key synthetic intermediate, 6, is easily prepared in racemic form using the synthetic protocol recently developed by Liotta and coworkers (Wilson et al, *Tetrahedron Lett.*, 31:1815, 1990). The conversion of racemic 6 to the corresponding uracil carborane (i.e., 1 and 3) is accomplished using the general route shown.

The 3'-thia and 3'-oxanucleosides can be resolved using lipase-mediated hydrolyses of appropriate 5'-acyl derivatives (Wilson et al, *Tetrahedron Lett.*, 31:1815, 1990), shown below:

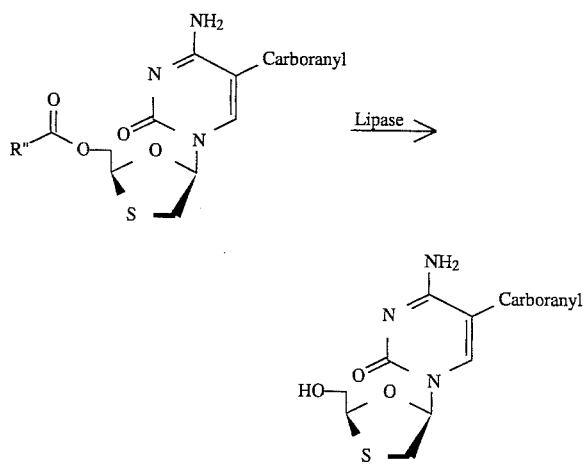

The enantiomers of cytidine analogues can also be resolved by cytidine/deoxycytidine deaminase since only the (+)-enantiomer are substrates for this enzyme. Having easy access to both enantiomers of these materials is important. Specifically, the extremely low toxicity of L-(−)—BCH-189 (3TC) and (−)-FTC may be attributed to the fact that these compounds are "unnatural" L-enantiomers. Thus, these materials are apparently accepted as substrates by cellular kinases, but are not recognized by most other key cellular enzymes and, therefore, may not interfere with normal cell functions.

Other compounds of formula I can be synthesized by replacing compound 5 in scheme I with the appropriate alternative. For example, when a compound in which X is other than O and Y is other than S is desired, one may simply replace starting material 5 with the analogous compound in which X and Y are the desired groups. Such starting materials are known in the art and are described in Bamford et al, *Tetrahedron Lett.*, vol. 32, pp. 271–274 (1991); Choi et al, *J. Amer. Chem. Soc.*, vol. 113, pp. 9377–9379 (1991); Jones et al, *Tetrahedron Lett.*, vol. 32, pp. 247–250 (1991); Norbeck et al, *Tetrahedron Lett.*, vol. 30, pp. 6263–6266 (1989); Peterson et al, *J. Med. Chem.*, vol. 34, pp. 2787–2797, (1991); Vince et al, *Biochem. Biophys. Res. Commun.* vol. 156, pp. 1046–1053; and J. Secrist et al, *J. Med. Chem.*, February 1992, which are incorporated herein by reference. Similarly, it is also possible to replace the TMS-5-iodocytosine employed in scheme I with an analogous substituted purine compound to prepare the compounds in which B is a purine. Such compounds are well known in the art.

In another embodiment, the present invention relates to sensitizing agents for boron neutron capture therapy having the formula II:

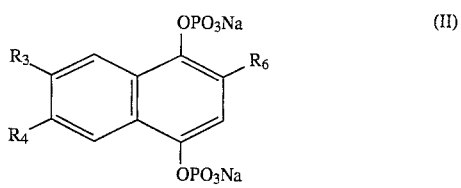

In which $R_3$ and $R_4$ are each, independently —H, —B(OH)₂, —B(OR₆)₂, or a carboranyl group having the formula —B₁₀H₁₀C₂R₈, wherein $R_8$ is —H, —OH, —CH₂OH, —CH₂X (wherein X is F, Cl, Br, I ) or —B₉C₂H₁₂⁻ (nidocarborane anion), provided that one of $R_3$ and $R_4$ is —H and the other of $R_3$ and $R_4$ is not —H. It is preferred that $R_3$ be —H and that $R_4$ is either —B(OH)₂ or

—$B_{10}H_{10}C_2H$.

The compounds of formula (II) may be prepared as shown in scheme II.

reduced and protected prior to boronation. Naphthoquinone containing a poly-boron moiety are prepared via coupling the iodo compound with trimethylsilyl acetylene in the

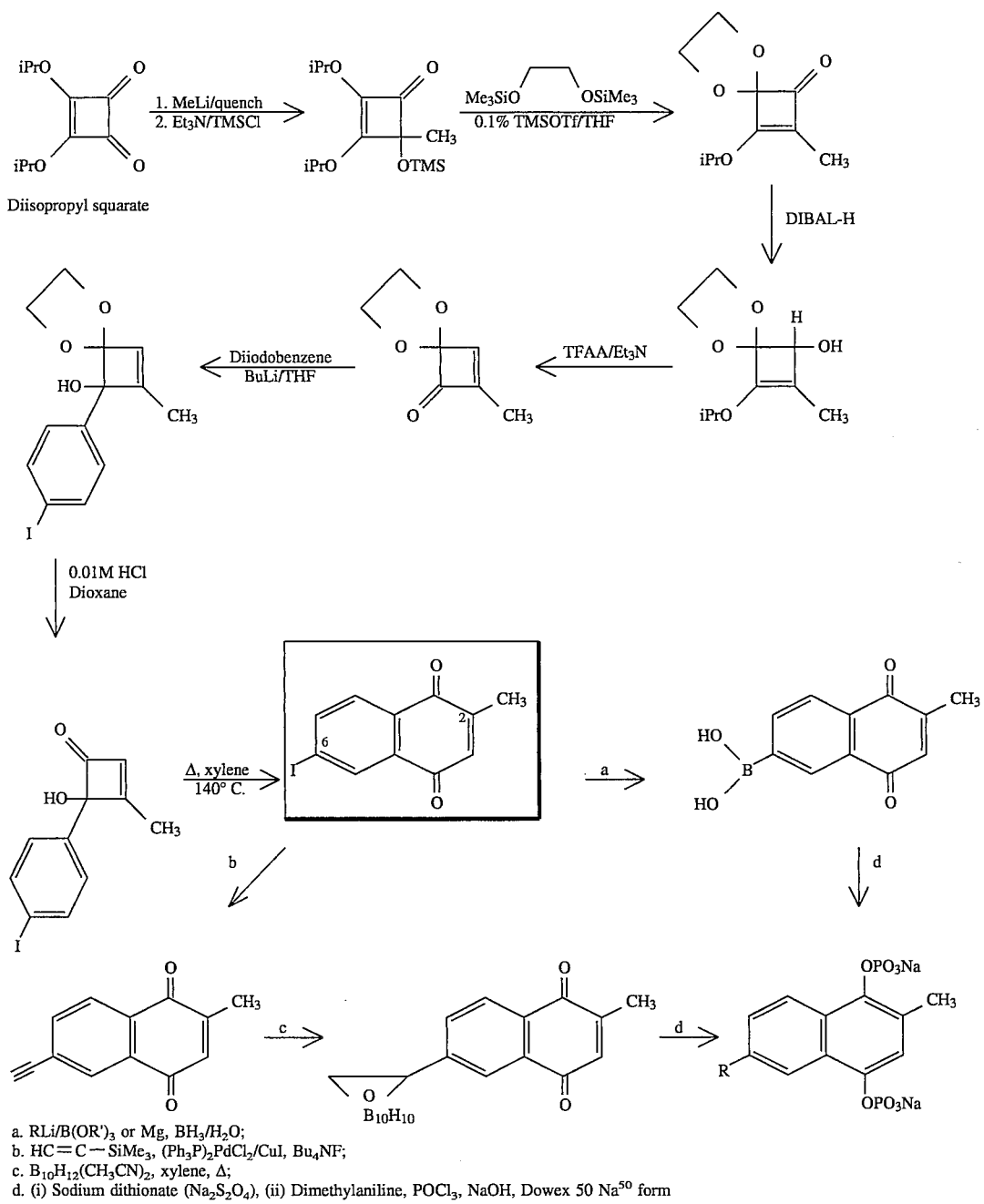

a. $RLi/B(OR')_3$ or Mg, $BH_3/H_2O$;
b. $HC \equiv C-SiMe_3$, $(Ph_3P)_2PdCl_2/CuI$, $Bu_4NF$;
c. $B_{10}H_{12}(CH_3CN)_2$, xylene, $\Delta$;
d. (i) Sodium dithionate ($Na_2S_2O_4$), (ii) Dimethylaniline, $POCl_3$, NaOH, Dowex 50 $Na^{50}$ form 6-Iodo-2-methyl-2,4-naphthoquinone required for the synthesis of boron containing naphthoquinones is prepared by starting with commercially available diisopropyl squarate applying the methodology developed by Liebeskind et al (Liebeskind et al, J. Org. Chem., 55, 5350–5358, 1990) and Enhsen et al (Enhsen et al, J. Org. Chem., 55, 1177–1185, 1990). 3-Methyl-4-p-iodophenyl-4-hydroxycyclobut-2-en-1-one on thermolysis gives the desired 6-iodo-2-methyl-1, 4-naphthoquinone required for boronation/hydroboration (see Scheme 1, above). Lithiation or Grignard reaction and boronation of 6-iodo-2-methyl-1,4-naphthoquinone provide the boronic acid. Alternately, the naphthoquinone can be presence of bis(triphenylphosphine)palladium(II) chloride and CuI followed by hydroboration with decarborane. The bis(disodium phosphate)-derivative of the two boron-containing naphthoquinones can easily be prepared, as shown. Compounds which contain a boron-containing substituent in the 7 position may be prepared by an analogous method, utilizing metadiiodobenzene. The capacity of this class of compounds to produce free radicals is markedly influenced by the type and position of the substituent on the naphthoquinone (ollinger et al, J. Biol. Chem., 266, 21496–21503, 1991).

It is to be understood that the present compounds of both formula I and II include pharmaceutically acceptable salts, such as acid addition salts of HCl and $H_2SO_4$, and salts in which an acidic hydrogen has been replaced by a cation such as $Na^+$, $K^+$, $\frac{1}{2}Mg^{+2}$, $NH_4^+$, and tetra-$C_{1-4}$-alkylammonium. It is also to be understood that when any of the present compounds exist as diastereoisomers or enantiomers, the present invention includes mixtures of such diastereoisomers and/or enantiomers as well as isolated diastereoisomers and resolved or optically enriched enantiomers.

In another embodiment, the present invention relates to pharmaceutical compositions which contain the present sensitizing agents of formula I or II. Such compositions may contain any acceptable carrier. Thus, the composition may be in a form suitable for oral or intravenous administration. If the composition is for oral administration it may be in liquid, solid, or gel form and may be in the form of a tablet, capsule, powder, or syrup. It is preferred that the composition be in a form suitable for intravenous administration, particularly intrathecal administration. In this case, the composition should be in a form suitable for injection, such as a solution or suspension in an acceptable liquid such as saline.

In a further embodiment, the present invention relates to a method of boron neutron capture therapy for treating cancer, preferably brain gliomas and melanomas, particularly preferably brain gliomas. Boron neutron capture therapy is discussed in Hatanaka et al, *Z. Neurol.*, vol. 204, pp. 309–332 (1973); Tolpin et al, *Oncology*, vol. 32, pp. 223–246 (1975); U.S. Pat. Nos. H505, 5,066,479, 5,021,572, 4,959,356, and 4,855,493; and Barth et al, *Cancer Res.*, vol. 50, pp. 1061–1070 (1990), Which are all incorporated herein by reference. Thus, in the present method, a patient in need thereof is treated with an effective amount of one or more to the present compounds and then exposed to neutrons, preferably thermal neutrons. For the compounds of formula I a suitable dose is 0.1 to 100 mg/kg of body weight in single dose, preferably 1 to 20 mg/kg of body weight in a single dose. For compounds of Formula II a suitable does is 0.1 to 200 mg/kg of body weight in a single dose, preferably 1 to 80 mg/kg of body weight in a single dose. It may be advantageous to pulse the dosage. In this case, the adjustments to the single and overall dosage amounts are within the abilities of one having ordinary skill.

In addition, the present compounds exhibit antiviral activity in cells infected HIV-1 (strain LAV), without the use of neutrons. Thus, these compounds have antiviral activity in the absence of neutrons. The results are shown in the Table below.

CYTOTOXICITY AND ANTI-HIV-1 ACTIVITY OF 5-CARBORANYL-PYRIMIDINE NUCLEOSIDES

| Compound | CEM $IC_{50}$, µM On day 6 | Vero $IC_{50}$, µM On day 3 | PBM $IC_{50}$, µM On day 6 | Anti-HIV-1[a] $EC_{50}$, µM On day 6 |
|---|---|---|---|---|
| 5-Carboranyl-2',3'-dideoxy-3'-thiauridine | 37.9 | 34.2 | >100 | 12.1 |
| 5'-O-Butyryl-5-carboranyl-3'-thia-2',3'-dideoxy-uridine | ND[b] | ND | ND | 6.4 |

[a]In Human PBM cells;
[b]ND = Not determined

Biological methods are described in Schinazi et al, *Antimicrob. Agents Chemother.*, vol. 34, pp. 1061–1067, (1990).

Other features of the invention will become apparent in the course of the following descriptions of exemplary embodiments which are given for illustration of the invention and are not intended to be limiting thereof.

EXAMPLES

I. Synthesis of the Compounds of Formula I

Prior to introduction of solvents and materials, the reaction vessel was evacuated and dried by heating in vacuo. After cooling, the atmosphere was replaced with argon. Addition or transfer of materials in the reaction was conducted under an argon atmosphere.

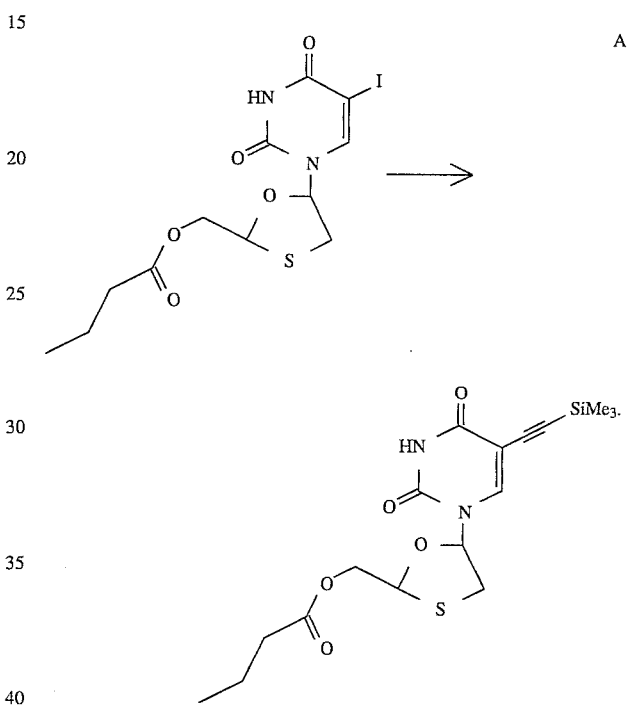

Into a flame-dried, argon-charged 25 ml three-necked round-bottomed flask, 21.6 mg (0.122 mmol, 0.1 equiv) of palladium chloride (Aldrich Gold label), 63.9 mg (0.244 mmol, 0.2 equiv) of triphenylphosphine and 46.45 mg (0.244 mmol, 0.2 equiv) of anhydrous cuprous iodide were transferred. A solution of 520 mg (1.22 mmol, 1.0 equiv) of iodide in 12.2 ml of anhydrous tetrahydrofuran followed by 0.345 ml (240 mg, 0.244 mmol, 2.0 equiv) of trimethylsilylacetylene and 0.51 ml (371 mg, 3.66 mmol, 3.0 equiv) of anhydrous triethylamine were added all at once. The clear reaction mixture was stirred at room temperature for 2 minutes after which the solution turned dark (warming up to about 45° C. was necessary to start the reaction in certain cases) and was qualitatively monitored for the disappearance of the UV-active iodide ($R_f$=0.34) and the appearance of a second UV-active component at $R_f$=0.38 ($SiO_2$, eluting with 50% hexanes and 50% ethyl acetate). The reaction mixture was stirred at room temperature for 4 h before reaching completion. To the dark mixture $SiO_2$ (flash chromatography) was added and the solvent evaporated under reduced pressure. The resulting solid was transferred into a column and chromatographed ($SiO_2$, eluting with 50% hexanes and 50% ethyl acetate) to give 360 mg (74% yield) of the desired alkyne as a yellowish solid (M.p. 122°–123° C.). $^1H$ NMR (360 MHz, $CDCl_3$)δ8.929 (bs, 1H, NH), 7.972(s, 1H, —C═C—H), 6.28 (dd, J=5.19, 4.35 Hz, 1H, —O—C H—N—), 5,36(dd, J=3.87,3.07 Hz, 1H, —O—CH—S—), 4.60(dd, J=12.54, 4.39 Hz, 1H, —CH—O-C=O), 4.44 (dd, J=12.53,2.88 Hz, 1H, —CH—O—C=O), 3.52(dd, J=12.34, 5.51 Hz, 1H, —CH—S—), 3.14(dd, J=12.35, 4.05 Hz, 1H, CH—S—), 2.50-2.36(m, 2H, —CH$_2$—C=O), 1.65(sextet, J=7.3 Hz, 2H, —CH$_2$—CH$_2$—C=O), 0.97 (t, J=7.42 Hz, 3H, CH$_3$—CH$_2$—), 0.233 (s, 9H, CH$_3$—Si—); $^{13}$C NMR (75 MHz, CDCl$_3$) δ 173.04, 160.83, 148.94, 142.45, 100.51, 100.09, 86.43, 83.99, 77.20, 63.29, 37.99, 35.73, 18.36, 13.61, 0.16; IR(neat) 3200, 3060, 2940, 2160, 1730, 1720, 1680, 1615, 1445, 1265, 1240, 1160, 900, 830, 720 cm$^{-1}$.

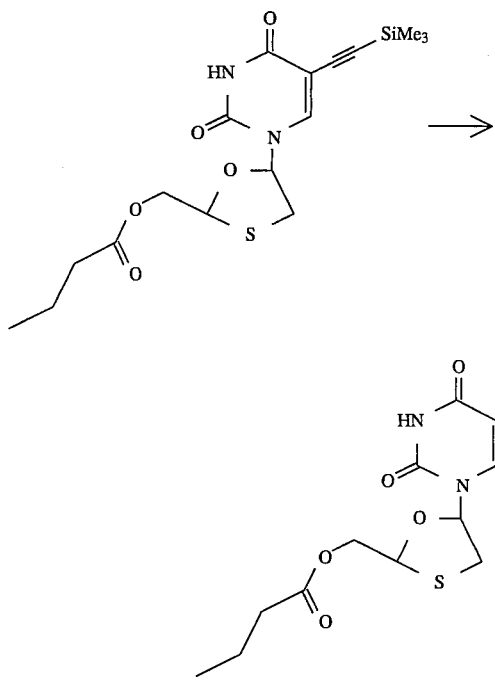

Into a flame-dried, argon-charged 25 ml two-necked round-bottomed flask, 335 mg (0.907 mmol, 1.0 equiv) of the alkyne in 9 ml of anhydrous tetrahydrofuran were added. The clear solution was stirred at room temperature and treated dropwise with 0.907 ml (237 mg, 0.907 mmol, 1.0 equiv) of tetrabutylammonium fluoride (1.0M solution in tertrahydrofuran, Aldrich). The clear reaction mixture was stirred at room temperature and was qualitatively monitored for the disappearance of the UV-active alkyne (R$_f$=0.38) and the appearance of a second UV-active component at R$_f$=0.20 (SiO$_2$, eluting with 50% hexanes and 50% ethyl acetate). The reaction mixture was stirred at room temperature for 2 h before reaching completion. To the clear mixture 500 mg of SiO$_2$ (flash chromatography) were added and the solvent evaporated under reduced pressure. The resulting solid was transferred into a column and chromatographed (SiO$_2$, eluting with 50% hexanes and 50% ethyl acetate) to afford 178 mg (65% yield) of the desired deprotected alkyne as a white solid (M.p. 126°-127° C.). $^1$H NMR (360 MHz, CDCl$_3$) δ 9.6-8.7 (bs, 1H, NH), 8.129 (s, 1H, —C=C—H), 6.295 (dd, J=5.19, 3.13 Hz, 1H, —O—CH—N—), 5.35 (t, J=3.03 Hz, 1H, O—CH—S—), 4.605(dd, J=12.69, 3.79 Hz, 1H, —CH—O— C=O), 4.44 (dd, J=12.66, 2.40 Hz, 1H, —CH—O—C=O), 3.57 (dd, J=12.65, 5.48 Hz, 1H, —CH—S—), 3.20 (dd, J=12.64, 2.96 Hz, 1H, —CH—S—), 3.185 (s, 1H, —C≡CH), 2.435 (t, J=7.43 Hz, 2H, —CH$_2$—CH$_2$—C=O), 1.67 (sextet, J=7.40 Hz, 2H, —CH$_2$—CH$_2$—C=O), 0.95 (t, J=7.39 Hz, 3H, CH$_3$—CH$_2$—); $^{13}$C NMR (75 MHz, CDCl$_3$) δ 173.06, 161.22, 149.02, 143.45, 98.92, 86.40, 84.91, 82.21, 74.65, 62.74, 38.77, 35.79, 18.32, 13.58; IR(neat) 3280, 3040, 2960, 2920, 2120, 1740, 1705, 1690, 1615, 1450, 1260, 1180, 1080, 1040, 730 cm$^{-1}$.

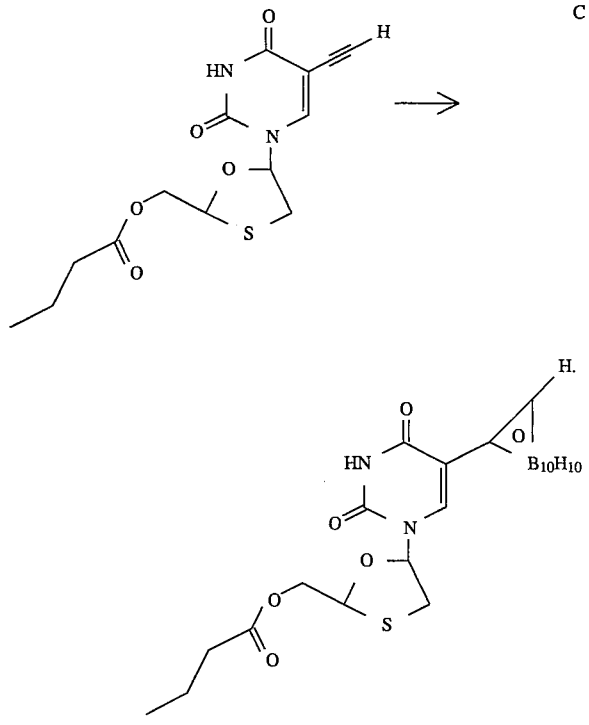

Into a flame-dried, argon-charged 50 ml two-necked round-bottomed flask, 170 mg (0.524 mmol, 1.0 equiv) of the alkyne in 20 ml of anhydrous toluene were added. The clear solution was stirred at room temperature and treated with 77 mg (0.629 mmol, 1.2 equiv) of decaborane-(14)(Aldrich) and dropwise addition of 0.74 ml (577 mg, 10.48 mmol, 20 equiv) of propionitrile (99% Aldrich). The slight yellow reaction mixture was heated to reflux and was qualitatively monitored for the disappearance of the UV-active alkyne (R$_f$=0.20) and the appearance of a second UV-active component at R$_f$=0.050 (SiO$_2$, eluting with 50% hexanes and 50% ethyl acetate). The reaction mixture was stirred at reflux temperature for 12 h before reaching completion. The reaction mixture was allowed to cool down to rooom temperature and the solvent evaporated under reduced pressure. The resulting crude solid was transferred into a column and chromatographed (SiO$_2$, eluting with 60% hexanes and 40% ethyl acetate) to afford 110 mg (47% yield) of the desired carborane ester as a slightly yellow oil. $^1$H NMR (360 MHz, CDCl$_3$)δ 9.75 (bs, 1H, NH), 8.047 (s, 1H, —C=C—H), 6.31 (dd, J=4.91, 4.11 Hz, 1H, O—C H—N—), 5.693 (bs, 1H, —B—CH), 5.36 (dd, J=5.44, 3.51 Hz, 1H, —O—CH—S—), 4.52 (dd, J=12.35, 5.64 Hz, 1H, —CH—O—C=O), 4.44 (dd, J=12.33, 3.44 Hz, 1H, —C H—O—C=O), 3.55 (dd, J=12.53, 5.59 Hz, 1H, —C H—S—), 3.15 (dd, J=12.50, 3.80 Hz, 1H, —CH—S—), 2.39 (t, J=7.42 Hz, 2H, —CH$_2$—CH$_2$—C=O), 2.40-1.80 (bm, 10H, —BH), 1.68 (sextet, J=7.41 Hz, 2H, —C H$_2$—CH$_2$—C=O), 0.96 (t, J=7.40 Hz, 3H, CH$_3$—CH$_2$—); $^{13}$C NMR (75 MHz, CDCl$_3$)δ 173.00, 160.38, 148.69, 141.79, 107.47, 86.52, 84.24, 69.48, 63.90, 57.92, 38.11, 35.74, 18.31, 13.54; IR (neat) 3200, 3070, 2960, 2940, 2570, 1740, 1700, 1680, 1620, 1460, 1370, 1280, 900, 730 cm$^{-1}$.

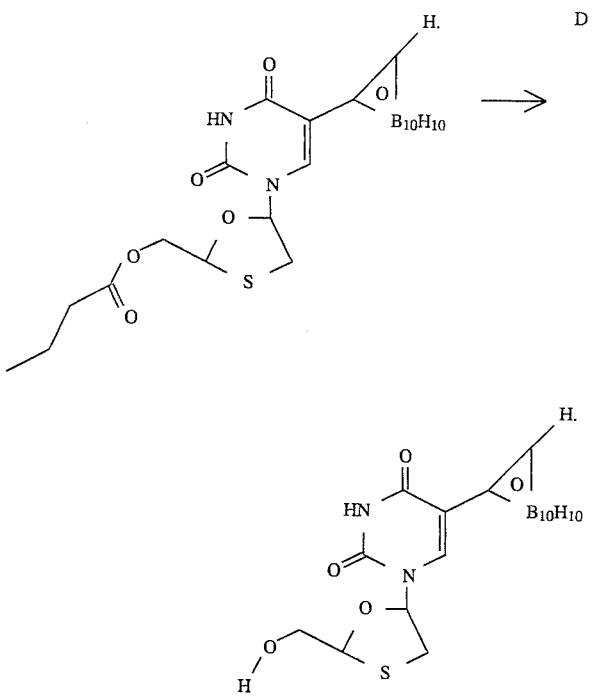

Into a flame-dried, argon-charge 25 ml round-bottomed flask, 99 mg (0.228 mmol, 1.0 equiv) of ester in 1.5 ml of methanol were added. The clear solution was stirred at room temperature and treated with 24.6 mg (0.455 mmol, 1.2 equiv) of sodium methoxide (Aldrich). The slightly yellow reaction mixture was stirred at room temperature and was qualitatively monitored for the disappearance of the UV-active ester ($R_f$=0.50) and the appearance of a second UV-active component at $R_f$=0.041 ($SiO_2$, eluting with 50% hexanes and 50% ethyl acetate). The reaction mixture was stirred at room temperature for 2 h before reaching completion. The reaction mixture was quenched with 1 ml of saturated aqueous ammonium chloride solution and the solvent evaporated under reduced pressure. The resulting crude solid was transferred into a column and chromatographed ($SiO_2$, eluting with 60% hexanes and 40% ethyl acetate) to afford 70 mg (84 % yield) of the desired carborane as a slight yellow oil. $^1$H NMR (360 MHz, $CD_3OD$) δ 8.386 (s, 1H, —C═C—H), 6.29 (dd, J=5.54, 2.19 Hz, 1H, —O—CH—N—), 5.896 (bs, 1H, —B—CH), 5.25 (t, J=3.79 Hz, 1H, —O—CH—S—), 3.96 (dd, J=12.34, 3.68 Hz, 1H, —CH—OH), 3.88 (dd, J=12.29, 3.98 Hz, 1H, —CH—OH), 3.53 (dd, J=12.70, 5.62 Hz, 1H, —CH—S—), 3.255 (dd, J=12.67, 2.32 Hz, 1H, —CH—S—), 2.80-1.40 (bm, 10H, —BH); $^{13}$C NMR (75 MHz, $CD_3$ OD) δ 162.53, 150.55, 144.22, 107.22, 90.12, 87.99, 72.40, 63.45, 59.91, 39.47; IR (neat) 3400, 3040, 2980, 2960, 2570, 1700, 1680, 1620, 1450, 1280, 1050, 910, 720 $cm^{-1}$.

II. Synthesis of the Compounds of Formula II

A. 2-3-Diisopropoxy-4-hydroxy-4-methylcyclobut-2-en-1-one

To a cooled solution of diisopropyl squarate (12.3 g. 56 mmol) in dry THF (250 ml) at −78° C. under $N_2$ was added dropwise MeLi (42 ml, 1.4M in $Et_2O$, 58.8 mmol) with stirring. The reaction mixture was stirred for 1 hr at −78° C. and then quenched with $H_2O$ (25 ml). The reaction mixture was diluted with $Et_2O$ (80 ml) and the organic layer separated. The aqueous layer was extracted with $CH_2Cl_2$ (3×50 ml) and the combined organic extract dried over $Na_2SO_4$. Concentration in vacuo followed by flash silica gel column chromatography using $Et_2O$ as eluent gave the title compound as a white crystalline solid (11.04 g, 92%). $^1$H NMR ($CDCl_3$) δ 4.89, 4.87 (overlap hept. J=6 Hz each, 2H), 2.60 (s, 1H), 1.50 (s, 3H), 1.41 (d, J=6 Hz, 3H), 1.39 (d, J=6 Hz, 3H), 1.29 (d, J=6 Hz, 3H), 1.26 (d, J=6 Hz, 3H).

B. 2-3-Diisopropoxy-4-methyl-4-(trimethylsiloxy)-cyclobut-2-en-1-one

To 2,3-diisopropoxy-4-hydroxy-4-methyl-cyclobut-2-en-1-one (8.3 g, 38.7 mol) dissolved in anhydrous $Et_2O$ (160 ml) was added triethylamine (16.2 ml, 116.1 mol) and chlorotrimethylsilane (7.4 ml, 58.1 mmol) with stirring at room temperature. The reaction solution was stirred overnight and then quenched with $H_2O$ (15 ml). The organic layer separated and the aqueous layer was extracted with $Et_2O$ (3×25 ml). The combined organic extract was dried over $Na_2SO_4$ and concentrated in vacuo. The residue was passed through a short silica gel column using hexane as eluent to yield the title compound as a colorless oil (9.41 g, 85%). $^1$H NMR ($CDCl_3$) δ4.83 4.82 (overlap hept, J=6 Hz each, 2H), 1.39 (s, 3H), 1.36(d, J=6 Hz, 3H), 1.34(d, J=6 Hz, 3H), 1.24(d, J=6 Hz, 3H), 1.21(d, J=6 Hz, 3H), 0.10 (s,9H).

C. 3-Isopropoxy-4-methyl-3-cyclobutene-1,2-dione 2-(Ethylene acetal)

To a magnetically stirred solution of 2,3-diisopropoxy-4-methyl-4-(trimethylsioloxy)-cyclobut-2-en-1-one (9.35 g, 32.6 retool) dissolved in dry THF (120 ml) was added bis(trimethylsiloxy)ethane (6.8 g, 33 retool) and a catalytic amount of fresh trimethylsilyl triflate (84 mg, 0.38 mmol). The reaction mixture was stirred for 15 min at room temperature (TLC indicated the absence of starting material) and passed through a plug of silica gel with ether as eluent. The eluent was concentrated in vacuo and the residue chromatographed on silica gel using hexanes:$Et_2O$ (3:2) as eluent gave the acetal as a white crystalline solid (5.3 g, 82%). $^1$H NMR ($CDCl_3$) δ4.73 (hept, J=6 Hz, 1H), 4.21-4.02 (m, 4H), 1.72(s, 3H), 1.41 (d, J=6 Hz, 6H).

D. 4-Hydroxy-2-isopropoxy-3-methyl-2-cyclobuten-1-one Ethylene acetal

3-Isopropoxy-4-methyl-3-cyclobutene-1,2-dione 2-(ethylene acetal) (5.3 g, 26.7 mmol) dissolved in dry $Et_2O$ (30 ml) at −20° C. was reduced with diisobutylaluminium hydride (30 ml, 1M in hexanes, 29.4 mmol). The reaction was followed by the disappearance of the starting material (TLC-hexanes:$Et_2O$, 7:3) and was complete in 10 min. Excess hydride was destroyed by the addition of water (15 ml) and the product extracted into ether (3×50 ml). The ether fraction was dried over $Na_2SO_4$ and concentrated in vacuo to give the hydroxy compound as a clear oil (5.0 g, 93%). $^1$H NMR($CDCl_3$) δ4.42 (hept, J=6 Hz, 1H), 4.14 (d, J=10 Hz 1H), 4.08-3.94 (m,4H), 1.75 (d, J=10 Hz, 1H), 1.72(s,3H), 1.28 (d, J=6 Hz, 3H), 1.27 (d, J=6 Hz, 6H).

E. 4-Methyl-3-cyclobutene-1,2-dione 2-(Ethylene acetal)

4-Hydroxy-2-isopropoxy-3-methyl-2-cyclobuten-1-one ethylene acetal (4.9 g, 24.4 mmol) dissolved in dry $Et_2O$ (30 ml) was treated with triethylamine (10.3 ml, 73.4 mmol), trifluoro acetic anhydride (4.5 ml, 31.7 mmol) at room temperature. The reaction mixture was stirred for 1 h and then saturated aqueous $NaHCO_3$ solution (50 ml) was added. After stirring the mixture for 30 min it was diluted with ether, and the organic fraction separated, dried over $Na_2SO_4$ and concentrated in vacuo. The crude product (2.8 g) was distilled in vacuo (0.2 mm Hg, 50° C.) to yield the desired product (0.61 g, 16%) as a clear oil, which was stored in the freezer. $^1$H NMR ($CDCl_3$) δ8.13 (s, 1H), 4.10-4.00(m, 4H), 1.85(s,3H).

F. 4-Hydroxy-4-p-iodophenyl-3-methyl-2-cyclobuten-1-one

Ethylene acetal

To p-diiodobenzene (0.7 g, 2.1 mmol) dissolved in dry $Et_2O$ (20 ml) at $-5°$ C. under $N_2$ atmosphere was added dropwise n-butyl lithium (0.88 ml, 1.6M in hexane, 1.4 mmol). The reaction mixture was stirred for 15 min and cooled to $-78°$ C. To this mixture a precooled solution of 4-methyl-3-cyclobutene-1,2-dione 2-(ethylene acetal) (160 mg, 1.1 mmol) in dry $Et_2O$ (20 ml) was added slowly, while maintaining the temperature at $-78°$ C., via a double end needle. After stirring for 20 min, the reaction mixture was quenched with 5% aqueous ammonium chloride (4 ml). Diluted with ether (10 ml), organic fraction separated, washed with brine (2×5 ml), dried over $Na_2SO_4$ and concentrated in vacuo. The residue was chromatographed on silica gel using hexanes:EtOAc (9:1) as eluent to yield the desired iodo compound (230 mg, 60%) as a white crystalline solid. $^1H$ NMR $(CDCl_3)$ $\delta 7.65$ (d, J=9 Hz, 2H), 7.20 (d, J=9 Hz, 2H), 6.00 (s, 1H), 4.00-3.76 (m, 4H), 3.10(s, 1H), 1.75(s,3H).

G. 4-Hydroxy-4-p-iodophenyl-3-methyl-2-cyclobuten-1-one

To a solution of 4-hydroxy-4-p-iodophenyl-3-methyl-2-cyclobuten-1-one ethylene acetal (80 mg, 0.23 mmol dissolved in $THF:H_2O$ (3:1, 8 ml) was added dropwise 1N $H_2SO_4$ (3 ml) at room temperature. The reaction mixture was stirred for 4 h. The mixture was then diluted with ether (10 ml), and the organic fraction was separated from the aqueous phase by repeated extractions with ether (2×5 ml). The ether layer was dried over $Na_2SO_4$ and concentrated in vacuo to give a pale yellow oil (62 mg, 87%). $^1H$ NMR $(CDCl_3)$ $\delta 7.80$ (d, J=9 Hz, 2H), 7.15 (d, J=9 Hz, 2H), 6.40 (s, 1H), 3.10 (s, 1H), 2.20 (s,3H).

H. 6-Iodo-2-methyl-1,4-naphthoquinone

4-Hydroxy-4-p-iodophenyl-3-methyl-2-cyclobuten-1-one (30 mg, 0.099 mmol) dissolved in freshly distilled xylenes (3 ml) was heated under reflux for 2 h under an argon atmosphere. The solvent was removed in vacuo and the residue chromatographed over silica gel using hexanes/$Et_2O$ (9:1) as eluent to give a yellow crystalline solid (10 mg, 34%). This is a known compound.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A compound having the formula II

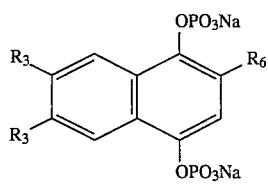

$R_3$ and $R_4$ are each, independently, —H, —$B(OH)_2$, —$B(OR_6)_2$ (wherein $R_6$ is a $C_{1-4}$ alkyl), or a carboranyl group —$B_{10}H_{10}C_2R_8$, wherein $R_8$ is —H, —OH, —$CH_2OH$, —$CH_2X$ (wherein X is F, Cl, Br, or I) or —$B_9C_2H_{12}^-$ (nidocarborane anion), provided that one of $R_3$ and $R_4$ is —H and the other of $R_3$ and $R_4$ is not —H, and pharmaceutically acceptable salts thereof.

2. The compound of claim 1, wherein $R_3$ is —H.
3. The compound of claim 2, wherein $R_4$ is —$B(OH)_2$ or

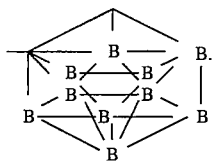

4. A pharmaceutical composition for boron neutron capture therapy, comprising an effective amount of a compound having formula II

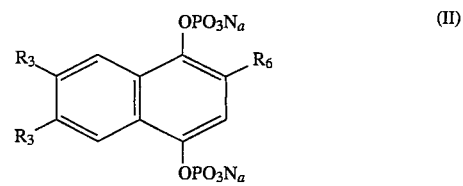

$R_3$ and $R_4$ are each, independently, —H, —$B(OH)_2$, —$B(OR_6)_2$ (wherein $R_6$ is a $C_{1-4}$ alkyl), or a carboranyl group —$B_{10}H_{10}C_2R_8$, wherein $R_8$ is —H, —OH, —$CH_2OH$, —$CH_2X$ (wherein X is F, Cl, Br, or I) or —$B_9C_2H_{12}^-$ (nidocarborane anion), provided that one of $R_3$ and $R_4$ is —H and the other of $R_3$ and $R_4$ is not —H, and pharmaceutically acceptable salts thereof.

5. A method of boron neutron capture therapy, comprising:

administering to a patient in need thereof an effective amount of a sensitizing agent which has the formula II,

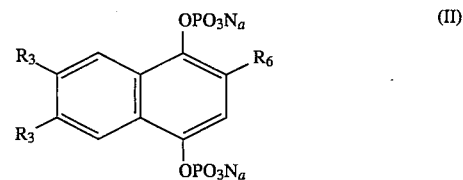

$R_3$ and $R_4$ are each, independently, —H, —$B(OH)_2$, —$B(OR_6)_2$ (wherein $R_6$ is a $C_{1-4}$ alkyl), or a carboranyl group —$B_{10}H_{10}C_2R_8$, wherein $R_8$ is —H, —OH, —$CH_2OH$, —$CH_2X$ (wherein X is F, Cl, Br, or I) or —$B_9C_2H_{12}^-$ (nidocarborane anion), provided that one of $R_3$ and $R_4$ is —H and the other of $R_3$ and $R_4$ is not —H, and pharmaceutically acceptable salts thereof.

6. The method of claim 5, wherein $R_3$ is —H.
7. The method of claim 6, wherein $R_4$ is —$B(OH)_2$ or

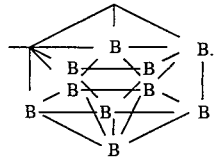

* * * * *

UNITED STATES PATENT AND TRADEMARK OFFICE
CERTIFICATE OF CORRECTION

PATENT NO. : 5,462,724
DATED : October 31, 1995
INVENTOR(S) : Raymond F. SCHINAZI It is certified that error appears in the above-indentified patent and that said Letters Patent is hereby corrected as shown below:

On the title page, Item [75], the Inventor should read:

--Raymond F. Schinazi, 1524 Regency Walk Dr., Decatur, Ga. 30033--

Item [19], please delete "et al".

Signed and Sealed this

Twenty-third Day of April, 1996

Attest:

BRUCE LEHMAN

Attesting Officer   Commissioner of Patents and Trademarks